US005684221A

United States Patent [19]

Forte et al.

[11] Patent Number: 5,684,221
[45] Date of Patent: Nov. 4, 1997

[54] MAMMALIAN MODEL OF A MALIGNANT DISORDER

[75] Inventors: Serene E. Forte, Hopkinton, Mass.; Patricia Bacha, Hollis, N.H.

[73] Assignee: Seragen, Inc., Hopkinton, Mass.

[21] Appl. No.: 242,044

[22] Filed: May 12, 1994

Related U.S. Application Data

[63] Continuation of Ser. No. 84,715, Jun. 29, 1993, abandoned, which is a continuation of Ser. No. 596,518, Oct. 12, 1990, abandoned.

[51] Int. Cl.$^6$ .................... A61K 48/00; A61K 49/00
[52] U.S. Cl. .................... 800/2; 800/DIG. 5; 424/9.2; 424/93.7; 424/573
[58] Field of Search .................... 800/2, DIG. 5; 424/9, 73, 77, 78, 520, 93.7, 93.71, 9.2, 573

[56] References Cited

FOREIGN PATENT DOCUMENTS

US91/07488   1/1992   WIPO.

OTHER PUBLICATIONS

Gillis et al., Nature, vol. 268, Issued Jul. 14, 1977, pp. 154–156.
Linden et al., BR. J. Cancer, vol. 58, Issued 1988, pp. 614–618.
Russell et al., Int. J. Cancer, vol. 44, Issued 1989, pp. 276–285.
Brunson et al., J. Nat'l. Cancer Inst. 61:1499, 1978.
Avent et al., J. Surgical Oncology 12:87, 1979.
Schirrmacher et al., Int'l. J. Cancer 23:233, 1979.
Miner et al., Cancer Res. 43:2063, 1983.
Brinster et al., Cell 37:367, 1984.
Steward et al., Cell 38:627, 1984.
Adams et al., Nature 318:533, 1985.
Diamantstein et al., Brit. J. Cancer 51:23, 1985.
Ruggiero et al., Brit. J. Cancer 51:37, 1985.
Hanahan et al., Nature 315:115, 1986.
Yamada et al., EMBO J. 6:2705, 1987.
Muller et al., Cell 54:105, 1988.
Hariharan et al., Mol. Cell. Biol. 9:2798, 1989.
Kiyokawa et al., Cancer Res. 49:4042, 1989.
Samid et al., Clinical Biotech. 1:21, 1989.
Lugasi et al., Int'l. J. Cancer 45:163, 1990.
Bacha et al., J. Exp. Med. 167:612–622 (1988).

Primary Examiner—Jasemine C. Chambers
Attorney, Agent, or Firm—Fish & Richardson, P.C.

[57] ABSTRACT

A method for producing a mouse having a systemic malignant disease which mimics a human IL-2 expressing. T-cell malignancy, which includes administering to a mouse a mixture of passaged cells comprising cancer causing cells, the mixture having been rendered cancer causing by in vivo passage of tumor inducing cells in athymic mice.

11 Claims, 2 Drawing Sheets

MAMMALIAN MODEL OF A MALIGNANT DISORDER

This is a continuation of application Ser. No. 08/084,715, filed Jun. 29, 1993, now abandoned; which is a continuation of application Ser. No. 07/596,518, filed Oct. 12, 1990, abandoned.

BACKGROUND OF THE INVENTION

This invention relates to animal models of human neoplasia.

The murine lymphosarcoma cell line RAW117 has been used to develop a model of large cell lymphoma (Brunson et al., *J. Nat'l Cancer Inst.* 61:1499, 1978). RAW117 is derived from spleen cultures of Balb/c mice infected with Abelson murine leukemia virus, which induces thymic-independent lymphosarcoma. Serial passage of this cell line has been employed to develop a metastasizing animal tumor model for large B-cell lymphoma (Miner et al., *Cancer Res.* 43:2063, 1983). Samid et al. (*Clinical Biotech.* 1:21, 1989) identified highly tumorigenic, metastatic variants of a human osteosarcoma cell line transformed by the ras oncogene by isolating tumors from athymic nude mice injected with the transformed cell line.

Other in vivo cancer models include the B16 mouse melanoma model (Avent et al., *J. Surgical Oncology* 12:87, 1979), a mouse mammary adenocarcinoma model in which the mouse harbors an activated oncogene (Steward et al., *Cell* 38:627, 1984; Muller et al., *Cell* 54:105, 1988), and transgenic mouse models for brain tumors (Brinster et al., *Cell* 37:367; 1984), pancreatic beta cell tumors (Hanahan, *Nature* 315:115, 1986), and B cell lymphoma (Adams et al., *Nature* 318:533, 1985).

Adult T cell leukemia/lymphoma (ATL) is an aggressive cancer associated with a median survival of less than one year. ATL cells express the high-affinity IL-b 2receptor. Existing models of IL-2 receptor-expressing T cell leukemias include the BALB/c-derived murine LB leukemia (Lugasi et al., *Int. J. Cancer* 45:163, 1990), which occurred spontaneously after infection with an IL-2 producing retrovirus, and a chemically-induced murine lymphoma (Schirrmacher et al., *Int. J. Cancer* 23:233, 1979. Upon injection into athymic mice, both cell types induce tumor formation at the site of injection, and LB leukemic cells will lead to a systemic disease in syngeneic mice (Ruggiero et al., *Brit. J. Cancer* 51:37, 1985).

SUMMARY OF THE INVENTION

In general, the invention features a method for producing a non-human mammal having a systemic malignant disease which mimics IL-2 expressing human T-cell malignancy, which involves administering to the mammal a mixture of cells including passaged cancer causing cells, the mixture having been rendered cancer causing by in vivo passage of tumor inducing cells in athymic mice. As used herein, "systemic malignant disease" means a malignancy that spreads beyond the tissues that are present at the site of induction of the tumor-inducing cells, and the term "malignancy" includes both lymphomas and leukemias.

In preferred embodiments, the mixture of cells is passaged in athymic nude mice, preferably, one to four times, most preferably three times, and passaged cells are isolated from the mice, the passaged cells being capable of forming malignant tumors in normal mice; and the malignancy comprises lymphoma. As used herein "passaged cells" means cells that have been introduced into an animal, are allowed to remain in the animal for a period of time during which they multiply, and are then removed from the animal. Preferably, the cancer causing cells expressing the IL-2 receptor are selectively killed by exposure to the IL-2/diphtheria toxin conjugate $DAB_{486}IL-2$; most preferably, the tumor inducing cells are ATCC accession No. CRLL10574 (i.e., CP3 cells). Preferably, at least 75% of the animals with a systematic malignant disease produced by administering CP3 cells develop tumors within 10 days of administration of the cells, and at least 40% of the animals with a systemic malignant disease die within 40 days of administering the cells.

The invention also features an animal, preferably a mouse, produced by the method described above, having a systemic malignant disease which mimics a human IL-2 expressing T cell malignancy which may preferably be lymphoma.

In another aspect, the invention features a method for selecting a therapeutic agent for treatment of a human IL-2 expressing T-cell malignancy, which includes providing an animal having a systemic malignant disease produced by the method of the invention, administering to the animal a malignancy-inhibiting amount of a therapeutic agent, and selecting an agent that inhibits the animal's malignant disease.

The invention provides an animal model for an IL-2 expressing human T-cell malignancy and a method by which to screen potential therapeutic agents for treatment of such a disease. This model is useful for determining cancer treatment in humans because lymphoma, e.g., occurs in a high proportion of the animals and closely mimics the tissue involvement and spread of, e.g., human lymphoma. Non-human mammals of the invention may be used as a model for any of several human IL-2 expressing T cell malignancies including IL-2 expressing lymphomas, e.g., adult T cell lymphoma, cutaneous T cell lymphoma, or IL-2 expressing leukemia, e.g., chronic T cell leukemia.

Other features and advantages of the invention will be apparent from the following description of the preferred embodiment thereof, and from the claims.

DESCRIPTION OF THE PREFERRED EMBODIMENTS

The drawings are first described.

Drawings

PRODUCTION OF MAMMALS HAVING A DISEASE THAT MIMICS HUMAN LYMPHOMA

Figure 1:
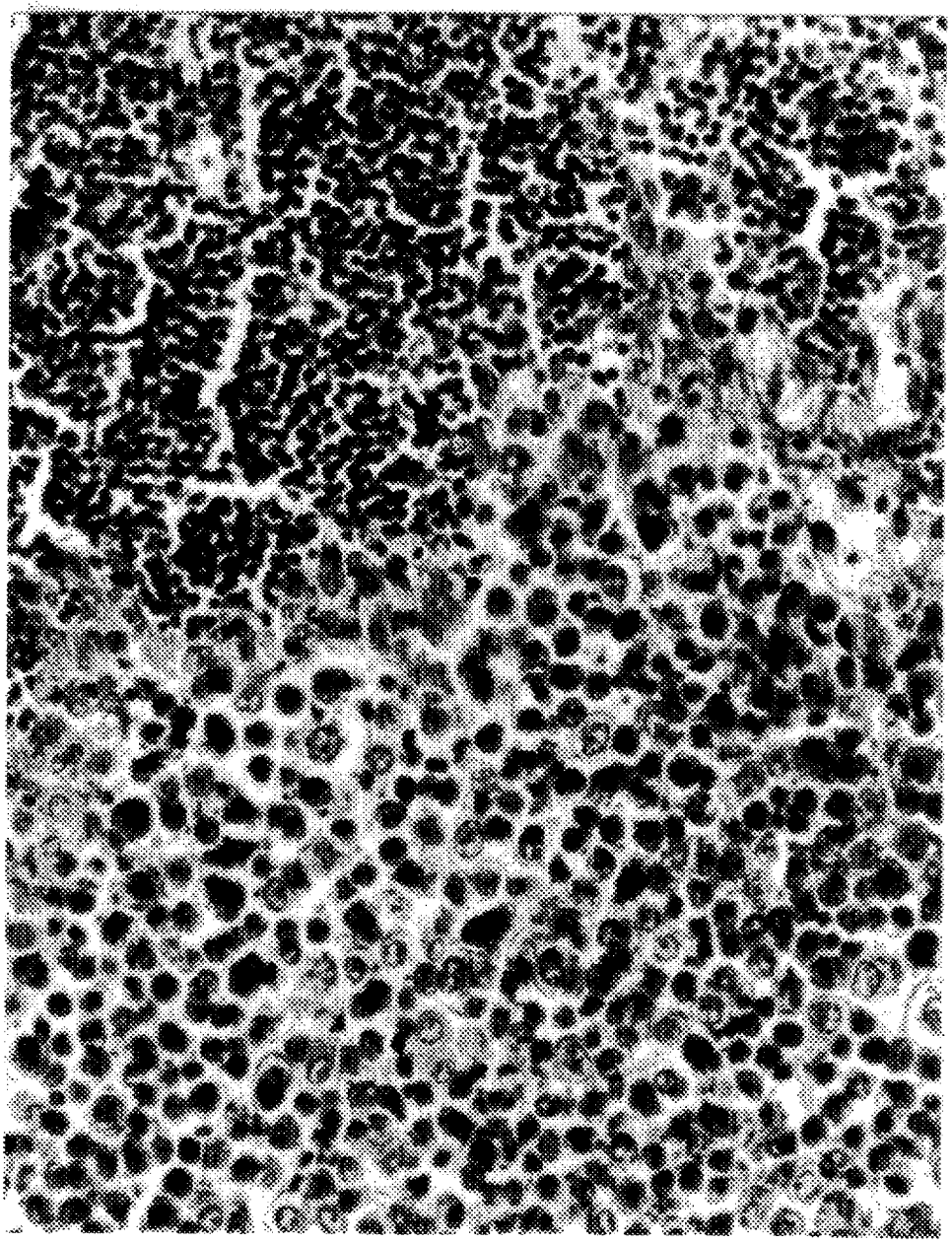
FIG. 1 illustrates a photograph of a hematoxylin and eosin stained section of a lymph node.

Non-human mammals of the invention are produced by administering to the mammal a mixture of passaged cells which have been rendered cancer causing by in vivo passage of tumor-inducing cells. Presented below is a detailed procedure for producing mice having a malignant disease which mimics human lymphoma, although the procedure can be applied to any non-human mammal, and to any IL-2 expressing T cell malignancy.

This particular model system is produced by injecting cells (CP3 cells) that were generated by serial in vivo passage of tumor producing cells (CTLL-transformant cells) into athymic mice. Serial in vivo passage was accomplished by injecting cells into the intraperitoneal cavity, allowing the injected cells to divide, selecting those mice with swollen abdomens who were injected with the fewest tumor-producing cells, collecting the ascites fluids of these mice, isolating cells from the pooled ascites fluid, and repeating the procedure until cells of the desired tumorigenicity are obtained. Tumorigenicity is measured by several criteria including total tumor mass, time to tumor formation and number of tumorigenic cells injected. Subsequent to injection of CP3 cells, a very high percentage of the injected mice develop the malignant disorder. Once a non-human mammal model of a malignant disorder such as human lymphoma is obtained, the mammal can be used to test potential therapies for human lymphoma.

Creation of CP3 Cells

CP3 (ATCC Accession No. CRLL10574) cells were produced by serial passage of CTLL-transformant cells in athymic nude mice. CTLL-transformant cells are CTLL-2 cells (an IL-2 dependent C57BL/6-derived cytotoxic T cell line, Gillis et al., Nature 268:154, 1977, that have been infected with a Moloney murine leukemia virus derived vector encoding IL-2. (Yamada et al., EMBO J. 6:2705, 1987). CTLL-transformant cells will proliferate, in vitro, in the absence of IL-2. CTLL-transformant cells will lead to tumor formation at the site of injection in athymic nude mice. Tumor formation in normal syngeneic C57BL/6 mice is poor with less than 20% of the mice affected. CTLL-transformant cells were maintained by subculturing at three to four day intervals in RPMI 1640 medium (GIBCO, Grand Island, N.Y.) supplemented with 25 mM HEPES, 2 µM glutamine, and 10% heat inactivated fetal calf serum (Hazelton Biologicals, Inc., Lenexa, Kans.).

Serial in vivo passage of CTLL transformants to obtain passages cells capable of causing a lymphoma-like malignant disorder when administered to an animal may be performed as follows.

On day one, four seven week old, female athymic nude mice (BR: athymic nu/nu, Harlan Sprague Dawley, Inc., Indianapolis, Ind.) were injected intraperitoneally with $10^7$ CTLL-transformant cells; on day 14, ascites fluid from each mouse was collected and pooled. Cells were isolated by centrifugation and washed with buffer (Dulbecco's Phosphate Buffered Saline, Gibco/BRL, Gaithersberg, Md.). The cells, now referred to as CP1 cells, were resuspended in buffer at $10^7$/ml.

Each of four athymic nude mice were then injected with $10^7$ CP1 cells; on day 7 ascites fluid was collected, and the cells were isolated, washed and resuspended. These cells are referred to as CP2 cells.

Each of two athymic nude mice were injected intraperitoneally with $10^6$ of these newly-isolated CP2 cells; on day 10, both mice had large ascites which were collected. The cells isolated from the ascites of these mice are CP3 cells.

Five mice were injected with $10^6$ CP3 cells. On day 10, all five of the mice had large ascites and large solid tumors throughout the mesoderm. The ascites fluid of these mice were collected; the cells isolated from the ascites, called CP4 cells, were washed and resuspended as above.

Nine athymic nude mice in groups of three were injected intravenously with $10^7$, $10^6$ or $10^5$ CP4 cells. All of the mice injected with $10^7$ or $10^6$ CP4 cells had extensive lymphatic tumors after 13 days, as did all of the mice injected with $10^5$ CP4 cells after 19 days.

Tumor Induction in the Model Mouse by CP3 Cells

CP3 cells are much more effective at inducing tumors than the original CTLL-transformant cells. When injected subcutaneously or intraperitoneally into athymic nude mice, CTLL-transformant cells will form tumors only at the injection site, and only a very small percentage of non-immunocompromised mice will develop tumors when injected intraperitoneally or subcutaneously with these cells. CTLL-transformant cells do not generate tumors when administered intravenously to either normal or athymic mice.

When as few as $10^6$ CP3 cells are injected intravenously into mice having non-compromised immune systems (e.g., C57BL/6), 90% of the animals show signs of observable tumor by day 10; death occurs in 50% of these animals by day 40.

The tumors induced by CP3 cells distribute lymphatically and are grossly observable by day 10 post-injection. Histological examination of a lymph node taken from a CP3-injected C57BL/6 mouse 36 days post-injection (FIG. 1) reveals that tumor cells predominate. Eventually, the normal architecture of the lymph node is destroyed and the tumor metastasizes to adjacent areas including the central nervous system. The significant differences between CTLL-transformant cells and CP3 cells is further illustrated by the fact that CTLL-transformant cells have a doubling time of 21 hours, while CP3 cells double in 12 hours.

Selection of Therapeutic Agents

Mice injected with CP3 cells can be used as an animal model of human lymphoma in order to select potential therapeutic agents for human lymphoma. Potential therapeutic agents includes anti-IL-2 receptor monoclonal antibodies; e.g., PC-61 (see below), IL-2 receptor specific cytotoxins, e.g., $DAB_{486}IL-2$ (see below), or any protein, drug, or agent which prevents IL-2 receptor function. Selection of a therapeutic agent may be performed as follows.

The effectiveness of each of two therapies directed against the IL-2 receptor, (1) PC-61, an anti-IL-2 receptor monoclonal antibody, and (2) $DAB_{486}IL-2$, an IL-2 receptor specific cytotoxin, was tested as described below.

Testing of PC-61 as a Therapeutic Agent

PC-61, a rat monoclonal IgG antibody directed against the murine IL-2 receptor (Lowenthal et al., J. Immunol. 135:3988, 1985), was prepared from culture supernatant fluids of PC-615.3 cells (ATCC No. TIB222) grown in serum free KC2000 media (Hazelton Biologics, Lenexa, Kans.). The antibody was concentrated in a stirred cell (Amicon Corp., Danvers, Mass.).

Figure 2:
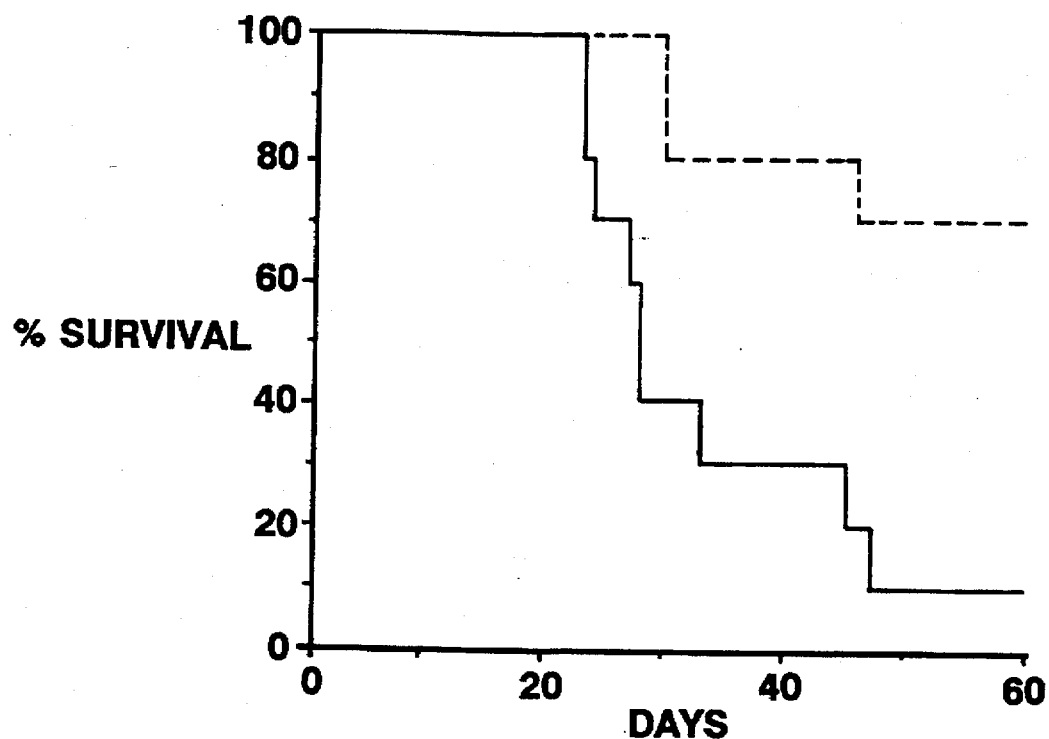
FIG. 2 is a graphical representation of the survival rate of mice injected with $10^6$ CP3 cells and either PC-61 (broken line) or Tris buffered saline (TBS) (solid line).

On day 0, two groups of C57BL/6 mice (10 per group) were injected in the tail vein with $10^6$ CP3 cells. On each of days 1 through 10, the test group received a daily intravenous injection of 20 µg PC-61; the control group received intravenous injections of TRIS buffered saline (TBS; 0.02M TRIS (pH8.2), 0.15M NaCl). The mice were monitored until day 60. FIG. 2 shows the results, in which the survival rates for test and control animals are plotted. For PC-61 treated mice (solid line), the day 60 survival rate was 70%; for TBS treated mice (broken line), the day 60 survival rate was 10%. Thus, PC-61 increases the survival rate in the model animals of the invention and is a potential therapeutic agent for human lymphoma.

Testing of $DAB_{486}IL$-2 as a Potential Therapeutic Agent

The cytotoxin $DAB_{486}IL$-2 is a fusion protein in which the region encoding the 50 amino acid receptor binding domain of diphtheria toxin has been replaced by amino acids 2 to 133 of mature human IL-2 (Williams et al., *Protein Eng.*, 1:493, 1987). Cells bearing the IL-2 receptor, including CTLL-2 cells, are sensitive to intoxication by $DAB_{486}IL$-2, which may occur by an IL-2 receptor mediated mechanism (Bacha et al., *J. Exp. Med.* 167:612, 1988). $DAB_{486}IL$-2 was produced in *E. coli* harboring the $DAB_{486}IL$-2 producing vector PSI100-31. The protein was purified by immunoaffinity chromatography and high pressure liquid chromatography (Williams et al., supra).

Figure 3:
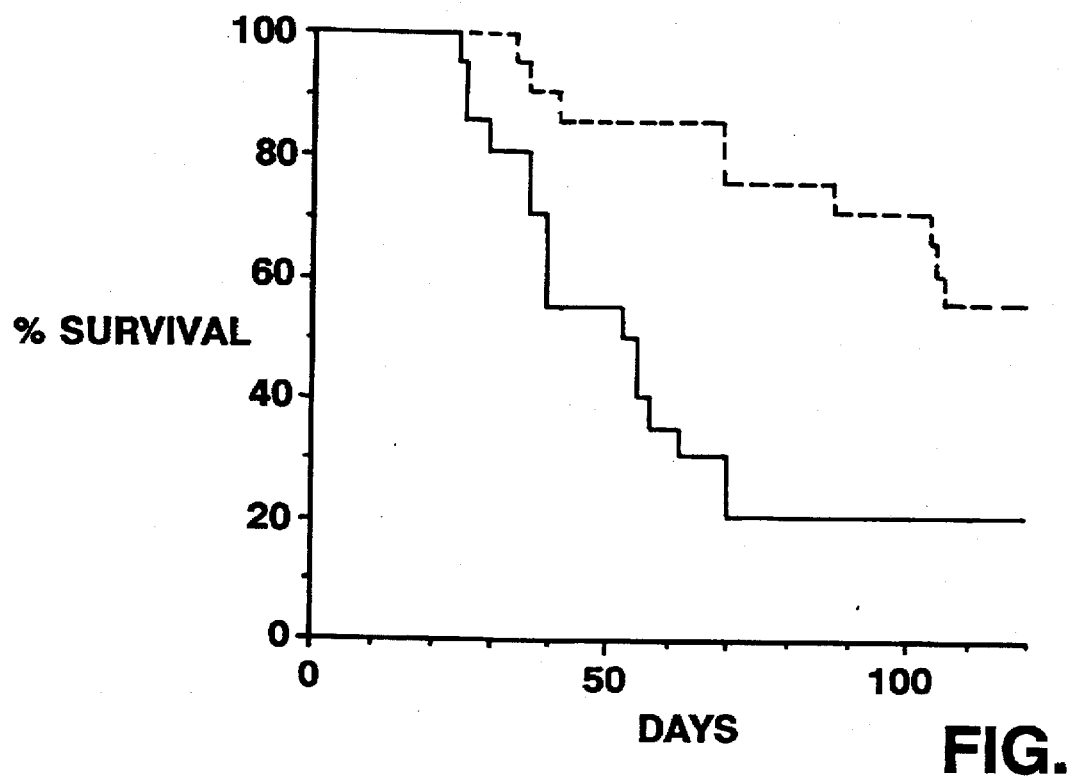
FIG. 3 is a graphical representation of the survival rate of mice injected with $10^6$ CP3 cells and either $DAB_{486}IL-2$ (broken line) or TRIS buffered saline (solid line).

On day 0, two groups of C57BL/6 mice (20 per group) were injected in the tail vein with $10^7$ CP3 cells. On each of days 1 through 10, the test group received a daily intravenous injection of 10 µg $DAB_{486}IL$-2 (FIG. 3, broken line); the control group received intravenous injections of TBS (FIG. 3, solid line). At day 120, the survival rate for the test group was 55%; the survival rate for the control group was 20%. Thus, $DAB_{486}IL$-2 increases the survival rate of model animals of the invention and is another potential therapeutic agent for human lymphoma.

Therapeutic agents can be selected by any criteria which can be applied to the model animal, including: increased life span, reduction in the size or number of tumors, limitation of the spread of tumors, limitation of the tissues invaded by tumors, reduction in metastasis, increase in time before the appearance of tumors, or increase in the period of time prior to metastasis.

Mechanism of Action

Therapeutic agents selected according to the invention may increase the survival rate of a model animal by any mechanism. For example, PC-61 or $DAB_{486}IL$-2 may have increased the survival rate of CP3 injected mice either through a direct cytotoxic effect or by growth inhibition caused by preventing binding of IL-2 to the IL-2 receptor.

USE

Non-human mammals of the invention may be treated with a malignancy-inhibiting, e.g., a lymphoma inhibiting amount of a therapeutic, agent, which amount may be determined by selecting a low and a high parameter, e.g., 1 µg/kg body weight to 1000 mg/kg body weight, and several amounts in between. The amount of the agent that results in the highest survival rate is, e.g., a lymphoma-inhibiting amount.

Deposit

CP-3 cells have been deposited with the American Type Culture Collection on Oct. 12, 1990, and bear the ATCC Accession No. CRLL1054. Applicants' assignee, Seragen, Inc., acknowledges its responsibility to replace these cells should they die before the end of the term of a patent issued hereon, and its responsibility to notify the ATCC of the issuance of such a patent, at which time the deposit will be made available to the public. Prior to that time the deposit will be made available to the Commissioner of Patents under the terms of 37 CFR §1.14 and 35 USC §112.

Other Embodiments

Other embodiments are within the following claims. The tumor inducing cells can be derived from any cell line, virally infected or not, from any tumor or from any other source that generates tumor inducing cells. Serial passaging of the cells in athymic mice can be accomplished by introducing the cells into the athymic animal at any convenient location by any convenient manner (e.g., subcutaneously, intradermally, intramuscularly or intravenously) and is not limited to injection into the intraperitoneal cavity.

We claim:

1. A method of producing a mouse having a systemic malignancy of the lymphatic tissue, said method comprising administering to a mouse with a non-compromised immune system a mixture of passaged cells comprising cells capable of causing a systemic malignancy of the lymphatic tissue in a non-immunocompromised mouse, said mixture of passaged cells being generated by the in vivo passage of CTLL-transformant derived cells in athymic mice.

2. The method of claim 1 wherein said mixture of passaged cells are generated by passaging between two and four times.

3. The method of claim 2 wherein said athymic mice are nude mice.

4. The method of claim 2 wherein said mixture of passaged cells are passaged three times.

5. The method of claim 1 wherein said malignancy is a lymphoma.

6. The method of claim 1, wherein said mixture of passaged cells are CP3 cells of ATCC No. CRLL 10574.

7. A mouse having a systemic malignancy of the lymphatic tissue produced by the method of claim 1.

8. The mouse of claim 7 Wherein said mouse has a malignancy of the central nervous system.

9. A method for selecting therapeutic agents for treatment of a human IL-2 expressing T-cell malignancy, said method comprising
   (a) providing the mouse of claim 7,
   (b) administering to said mouse a candidate therapeutic agent,
   (c) monitoring said mouse for occurrence or growth of tumors, and
   (d) identifying a said candidate therapeutic agent as a therapeutic agent if it reduces the occurrence or growth of said tumors compared to an otherwise identical untreated control mouse.

10. A method for selecting therapeutic agents for treatment of a human IL-2 expressing T-cell malignancy, said method comprising
    (a) providing the mouse of claim 7,
    (b) administering to said mouse a candidate therapeutic agent, and
    (c) identifying a said candidate therapeutic agent as a therapeutic agent if it increases the life span of said mouse compared to an otherwise identical untreated control mouse.

11. A composition comprising CP3 cells (ATCC No. CRLL 10574), said cells being capable of causing a systemic malignancy of the lymphatic tissue in a non-immunocompromised mouse.

* * * * *

UNITED STATES PATENT AND TRADEMARK OFFICE
CERTIFICATE OF CORRECTION

PATENT NO.   : 5,684,221
DATED        : November 4, 1997
INVENTOR(S)  : Forte et al.

It is certified that error appears in the above-identified patent and that said Letters Patent is hereby corrected as shown below:

Column 1, line 37, change "IL-b 2receptor" to --IL-2 receptor--
Column 1, line 43, insert --)-- immediately after "1979."
Column 2, line 6, change "CRLL10574" to --CRL10574--
Column 2, lines 16, 34, 35, 36, 37, and 67 change each occurrence of "T cell" to --T-cell--
Column 2, line 56, change "TRIS" to --Tris--
Column 3, line 21, change "CRLL10574" to --CRL10574--
Column 3, line 63, change "were" to --was--
Column 5, line 56, change "CRLL1054" to --CRL10574--
Column 6, lines 31 and 59, change "CRLL 10574" to --CRL10574--
Column 6, line 34, change "Wherein" to --wherein--

Signed and Sealed this

Twenty-third Day of June, 1998

Attest:

BRUCE LEHMAN

Attesting Officer          Commissioner of Patents and Trademarks